United States Patent [19]
Modak et al.

[11] Patent Number: 5,487,896
[45] Date of Patent: Jan. 30, 1996

[54] ANTIMICROBIAL GLOVE COMPRISING A RAPID RELEASE MATRIX SYSTEM FOR ANTIINFECTIVE AGENT DELIVERY

[75] Inventors: Shanta Modak, River Edge, N.J.; Lester Sampath, Nyack, N.Y.

[73] Assignee: Trustees of Columbia University In The City of New York, New York, N.Y.

[21] Appl. No.: 241,474

[22] Filed: May 12, 1994

[51] Int. Cl.$^6$ ........................................ A61K 7/043
[52] U.S. Cl. ........................ 424/402; 424/404; 424/405
[58] Field of Search ................................ 424/402, 404, 424/405

[56] References Cited

U.S. PATENT DOCUMENTS 4,853,978  8/1989  Stockum ........................... 2/167
5,133,090  7/1992  Modak et al. ..................... 2/168

Primary Examiner—Thurman K. Page
Assistant Examiner—Sharon Howard
Attorney, Agent, or Firm—Brumbaugh, Graves, Donohue & Raymond

[57] ABSTRACT

The present invention relates to an antimicrobial glove which exhibits rapid release of the antiinfective agent chlorhexidine. It is based, at least in part, on the discovery that when a slurry having a high ratio of chlorhexidine to starch lubricant, where the percentage of starch lubricant is between 7 and 10 percent, is used to coat the inner surface of a latex glove, the resulting antimicrobial activity is available surprisingly quickly, within about 30 seconds to one minute of exposure to liquid. This rapid release of antiinfective agent may be explained by the presence, in gloves according to the invention, of two matrix layers, one comprising the starch lubricant, the other comprising latex in the body of the glove in immediate apposition to the lubricant, both of which are supersaturated with chlorhexidine.

16 Claims, No Drawings

ANTIMICROBIAL GLOVE COMPRISING A RAPID RELEASE MATRIX SYSTEM FOR ANTIINFECTIVE AGENT DELIVERY

INTRODUCTION

The present invention relates to a glove which provides antimicrobial activity within 30 seconds to 1 minute of exposure to liquid. Gloves according to the invention may be used to protect the wearer against bacterial or viral infection.

BACKGROUND OF THE INVENTION

Surgical and examination gloves perform a barrier function providing separation between a patient and a health care worker. In fulfilling this function, the gloves act to block the introduction of infectious agents, particularly bacteria and fungi, from the hands of the health care worker into a surgical incision or wound of the patient. In this regard, it has been recognized that bacteria present in pores of a health care worker's hands frequently survive antibacterial scrubbing to be released with perspiration into the interior of the glove. These bacteria pose a significant risk of infection for the patient if a tear or hole in the glove allows their release. Thus, antimicrobial gloves have been proposed with the intention of killing these released bacteria within the glove. U.S. Pat. No. 4,853,978 to Stockum.

The barrier function of the gloves also serves to protect the health care worker from pathogenic agents, particularly those present in the blood or other body fluids of the patient. Of particular significance in this regard are viruses, such as HIV, the virus causing Acquired Immunodeficiency Syndrome (AIDS), and Hepatitis B virus (HBV) which may even penetrate through a glove that is not actually perforated, but merely stretched. Agents which are effective against these viral pathogenic agents, however, are less common than those that will provide an effect against simple skin bacteria or fungi and must frequently be present at much higher levels to be efficacious. This can cause difficulties for the wearer whose skin is in contact with high levels of antiinfective agent, sometimes for hours at a time. It would therefore be highly advantageous to provide gloves in which an effective virucidal agent were maintained in a "ready" state, available for quick or even instant release as needed to counter the effects of possible viral contamination.

The Stockum patent cited above provides a partial but incomplete solution to this problem. Stockum discloses gloves having an interior coating of polyurethane, starch and chlorhexidine. Chlorhexidine has the ability to kill the AIDS virus and HBV as shown in prior commonly assigned U.S. patent application Ser. No. 07/385,290, which is incorporated herein by reference. The release rates reported by Sotckum, i.e., release from the coating over several hours, are not quick enough, however, to provide meaningful protection from viral pathogens. Moreover, we have found that gloves made by dipping cured gloves in an antimicrobial preparation suffer from significant activity loss on storage, and thus from poor reliability.

U.S. Pat. No. 5,133,090 describes an antimicrobial glove in which adsorption sites for antiinfective agent in the lubricating agent or in the glove material itself are blocked. Gloves prepared according to U.S. Pat. No. 5,133,090 deliver an effective amount of antiinfective agent within ten minutes of exposure to liquid.

It is the objective of the present invention to provide surgical or examination gloves which even more rapidly release effective antiviral amounts of an antiinfective agent upon exposure to liquid, and which retain this ability over periods of prolonged storage.

SUMMARY OF THE INVENTION

The present invention relates to an antimicrobial glove which exhibits rapid release of the antiinfective agent chlorhexidine. It is based, at least in part, on the discovery that when a slurry having a high ratio of chlorhexidine to starch lubricant, where the percentage of starch lubricant is between 7 and 10 percent, is used to coat the inner surface of a latex glove, the resulting antimicrobial activity is available surprisingly quickly, within about 30 seconds to one minute of exposure to liquid. This rapid release of antiinfective agent may be explained by the presence, in gloves according to the invention, of two matrix layers, one comprising the starch lubricant, the other comprising latex in the body of the glove in immediate apposition to the lubricant, both of which are supersaturated with chlorhexidine.

DETAILED DESCRIPTION OF THE INVENTION

The present invention relates to an antimicrobial glove, having improved drug release properties, which inactivates fluid-borne, especially blood borne, pathogens within 30 seconds to 1 minute of contact with fluid.

In particular, the present invention provides for an antimicrobial glove comprising chlorhexidine in a form which provides effective antimicrobial action which is releasable between 30 seconds and 1 minute of exposure to liquid. Effective antimicrobial action, as used herein, refers to an amount of antimicrobial action which effectively prevents successful infection by a viral, bacterial or fungal pathogen. As a standard, but not by way of limitation, effective antimicrobial action refers to an ability to achieve 100% kill of *Staphylococcus aureus* within one minute of exposure of the glove to liquid containing the bacteria.

Antimicrobial gloves according to the invention comprise a bilayer drug release matrix system. According to the invention, the first layer on the inner side of the glove is a lubricant/chlorhexidine matrix and the second layer is the latex/chlorhexidine matrix formed from the body of the glove itself, which contains readily available bioactive amounts of chlorhexidine.

The lubricant matrix comprises a starch/chlorhexidine matrix which rapidly releases antimicrobial amounts of chlorhexidine when exposed to body fluids. In each glove, the amount of chlorhexidine in the chlorhexidine/starch matrix ranges from 8 mg to 20 mg and the amount of starch ranges from 200 mg to 500 mg (preferably 300–400 mg).

The latex/chlorhexidine matrix comprises chlorhexidine which is taken up from the slurry as well as chlorhexidine which has migrated from the starch/chlorhexidine lubricant layer, to supersaturate binding sites for chlorhexidine in the latex body of the glove.

Both lubricant and latex matrix systems may comprise a cationic surfactant, such as didecyldimethylammonium chloride (Bardac), which further enhances the instant release of chlorhexidine. Any tackiness of gloves resulting from the chlorhexidine may be prevented by the addition of silicone or other lubricants which do not interfere with the instant release of chlorhexidine or its efficacy.

Gloves for further processing according to the present invention may be prepared substantially according to the method set forth in U.S. Pat. No. 5,133,090, which is incorporated, by reference, in its entirety herein. The bilayer matrix, according to the present invention, is produced by applying, to the inner surface of the glove, a slurry comprising:

| | | |
|---|---|---|
| Chlorhexidine | 4–6% | (preferably 5%) |
| Cornstarch | 7–10% | (preferably 8%) |

In preferred specific embodiments of the invention the slurry may further comprise:

| | | |
|---|---|---|
| Bardac and/or | 0.02–0.4% | (preferably 0.2%), |
| Silicone Emulsion | 0.5–2% | (preferably 0.6%). |

For example, and not by way of limitation, hand-shaped glove forms may be prepared for use by rinsing them with 0.6% ammonium hydroxide and drying at 100° C. for 20 minutes. The dried glove forms may then be dipped in a coagulant bath (280 g of a mixture of calcium nitrate and calcium carbonate, and 1 ml Surfynol TG surfactant pre 4000 ml of coagulant) at a temperature of 50° C. for 24 seconds. The coagulant coated glove forms may then be dried for 75 seconds at 100° C. to prepare them for dipping in a latex dipping solution. The dip in the latex dipping solution may be sustained for a duration of about 15 seconds, after which the resulting partially formed gloves may be dried at 100° C. for five minutes. The partially formed gloves may then be mechanically rolled to make a bead on the cuff and then may be immersed in a water bath at 80° C. for about 3 minutes to leach out unwanted chemicals.

After the leaching step, an inner coating may be applied by dipping the leached glove into an aqueous slurry containing 4–6% chlorhexidine (preferably 5%) (e.g. chlorhexidine gluconate, "CHG"), 7–10% cornstarch (preferably 8%), 0.02–0.4% Bardac (preferably 0.2%), and, optionally, 0.5–2% (preferably 0.6%) silicone emulsion.

After dipping in the slurry, the glove may be dried in an oven at 100° C. for about one hour.

It may be expected that a certain amount of chlorhexidine applied via the slurry may be adsorbed by the latex matrix of the glove, thereby forming a supersaturated latex matrix. As a result of this adsorption, the amount of chlorhexidine residing in the lubricant matrix layer may be expected to be less than the amount present in the slurry and may be, for example and not by way of limitation, between 8 mg and 20 mg per glove. The fact that chlorhexidine is adsorbed into the latex matrix, and that releasable chlorhexidine is present in the latex matrix, is believed to be important for achieving the rapid release of chlorhexidine.

Gloves according to the present invention may be useful in protecting the wearer from microbes including, but not limited to, bacteria such as *Staphylococcus aureus*, viruses such as hepatitis viruses and human immunodeficiency viruses, and fungi such as yeast.

The gloves described above have been observed to retain their bioactivity even after aging. The stability of the bioactivity of the gloves was determined by testing gloves prepared in accordance with the invention in vivo after accelerated aging (100° C. for 24 hours) as well as after slow aging (37° C. for 6 months). It has been determined that the results of efficacy tests carried out in vitro do not necessarily match those obtained from in vivo experiments. This may be due to binding of drug to the skin, with consequent decreased bioavailability. Therefore the actual efficacy of an antimicrobial glove is preferably tested in vivo in presence of blood, except where the microbe to be tested is so pathogenic as to create an unreasonable health risk.

EXAMPLE: RAPID RELEASE OF ANTIMICROBIAL ACTIVITY

The efficacy testing was carried out in human volunteers. The following slurries, set forth in Table 1, were used to make four different varieties of gloves for testing.

TABLE 1

| Slurries Used to Prepare Gloves | | |
|---|---|---|
| Group | CHG/Starch Ratio | Other Ingredients |
| 1 | 0 | 0.2% Bardac + 0.6% Silicone |
| 2 | 0.25 | 0.2% Bardac + 0.6% Silicone |
| 3 | 0.5 | 0.2% Bardac + 0.6% Silicone |
| 4 | 0.625 | 0.2% Bardac + 0.6% Silicone |
| 5 | 1200 μg CHG (Amount detected in starch matrix) in control glove finger | |

After washing their hands with soap and water and disinfecting them with 70% isopropanol, each volunteer donned a pair of gloves After 30', 100 μL of blood containing $10^5$ CFU *Staphylococcus aureus*/ml was introduced into each glove finger through a small cut at the top of the glove finger After different time periods (2', 1' and 30 seconds), 0.9 ml of chlorhexidine-inactivating (LTSB) media was added to each finger to extract the contents. A 0.2 ml aliquot was then subcultured on trypticase soy agar plates and after 24 hours of incubation the colony counts were determined. The results are set forth in Table 2.

TABLE 2

| Antimicrobial Evaluation in Human Volunteers | | | |
|---|---|---|---|
| | % Inactivation at | | |
| Group | 2' | 1' | 30" |
| 1 | 0 | — | — |
| 2 | 98 | — | — |
| 3 | 98.8 | — | — |
| 4 | 100 | 100 | >99.0 |
| 5 | 96.2 | — | — |

When the same amount of chlorhexidine which was detected in the inner starch layer in group #3 glove fingers was taken from a standard chlorhexidine solution and tested for efficacy, only a 96.2% reduction in CFU was seen. This indicates that the efficacy of gloves from group #3 results from release of either additional chlorhexidine from the latex matrix, synergism with Bardac or both.

EXAMPLE: PROTECTIVE ACTIVITY AGAINST STAPHYLOCOCCUS AUREUS 0.1 ml aliquots from the following groups of solutions were evenly spread on the inside of normal glove fingers and immediately 0.1 ml blood containing $10^5$ CFU *Staphylococcus aureus*/ml was added to each finger. After 1', 0.9 ml chlorhexidine inactivating media was added and mixed. Aliquots were subcultured for determining the colony counts.

TABLE 3

| GROUP | Antibacterial Activity (CFU/Finger) |
| --- | --- |
| A. Control | $9 \times 10^3$ |
| B. Aliquot of CHG-Starch suspension containing the same amount of CHG/Starch in a glove finger from Group 3 | $6 \times 10^3$ |
| C. B + Bardac in Same Proportions as in glove finger of Group 3 | 12 |
| D. Same amount in a glove finger | $9.4 \times 10^3$ |
| E. Same as C + Silicone | 10 |
| F. B + Silicone | $4.6 \times 10^3$ |
| G. Same amount of CHG as in the starch matrix of glove finger but without starch | 350 |
| H. Glove finger from group 3 | 2 |
| I. Glove finger from group 3 after rinsing with saline to remove CHG/Starch matrix | 63 |
| J. Same amount of CHG as in starch matrix + instantly releasable CHG in latex matrix | 30 |

It appears from the above data that a starch/chlorhexidine matrix alone may not release enough chlorhexidine to inactivate bacteria even if the ratio is above 0.05, as in group 3 gloves. However when Bardac is added to the complex, 99.8% kill is seen. This indicates that Bardac permits the release of chlorhexidine from the starch. Bardac may also be acting synergistically with chlorhexidine because the percent kill of chlorhexidine alone (Group G) is lower than that of Group C. The glove finger showed 100% efficacy. The washed glove finger also showed significant efficacy which may be the result of release of CHG from the surface of latex matrix which is saturated with CHG and Bardac.

Thus, it appears that the efficacy of the antimicrobial glove in inactivating blood-borne pathogen within 1' results from the release of a cidal amount of a drug from (1) the release of bound CHG by Bardac from the lubricant matrix (2) the release of CHG from the latex matrix and/or (3) synergistic action of Bardac with CHG.

According to the present invention, comparable antimicrobial effects can be achieved in other medical devices, such as condoms, by creating a lubricant/chlorhexidine and latex/chlorhexidine matrix system as set forth above.

Various publications are cited herein which are hereby incorporated by reference in their entirety.

We claim:

1. An antimicrobial glove comprising chlorhexidine in a bilayer which comprises a latex/chlorhexidine matrix layer, and a starch/chlorhexidine matrix layer wherein the starch/chlorhexidine matrix comprises between 200 mg and 500 mg of starch and between 8 and 20 mg of chlorhexidine gluconate, the antimicrobial glove providing effective antimicrobial action which is releasable within between 30 seconds and 1 minute of exposure to liquid.

2. The antimicrobial glove according to claim 1 which further comprises didecyldimethylammonium chloride.

3. The antimicrobial glove according to claim 1 which further comprises didecyldimethylammonium chloride.

4. The antimicrobial glove according to claim 1 which further comprises a silicone lubricant.

5. The antimicrobial glove according to claim 1 which further comprises a silicone lubricant.

6. The antimicrobial glove according to claim 1 which further comprises a silicone lubricant.

7. The antimicrobial glove according to claim 2 which further comprises a silicone lubricant.

8. The antimicrobial glove according to claim 3 which further comprises a silicone lubricant.

9. An antimicrobial glove prepared by a process comprising applying, to a latex glove body, an aqueous slurry comprising between 4 and 6 percent chlorhexidine gluconate and between 7 and 10 percent starch.

10. The antimicrobial glove according to claim 9 in which the slurry further comprises between 0.02 and 0.4 percent didecyldimethylammonium chloride.

11. The antimicrobial glove according to claim 9 in which the slurry further comprises between 0.5 and 2 percent of a silicone emulsion.

12. The antimicrobial glove according to claim 10 in which the slurry further comprises between 0.5 and 2 percent of a silicone emulsion.

13. An antimicrobial glove prepared by a process comprising applying, to a latex glove body, an aqueous slurry comprising about 5 percent chlorhexidine gluconate and about 8 percent starch.

14. The antimicrobial glove according to claim 13 in which the slurry further comprises about 0.2 percent didecyldimethylammonium chloride.

15. The antimicrobial glove according to claim 13 in which the slurry further comprises about 0.6 percent of a silicone emulsion.

16. The antimicrobial glove according to claim 14 in which the slurry further comprises about 0.6 percent of a silicone emulsion.

* * * * *

UNITED STATES PATENT AND TRADEMARK OFFICE
CERTIFICATE OF CORRECTION

PATENT NO. : 5,487,896

DATED : January 30, 1996

INVENTOR(S) : Modak et al.

It is certified that error appears in the above-identified patent and that said Letters Patent is hereby corrected as shown below:

Col. 1, line 52, "Sotckum" should read --Stockum--;

Col. 3, line 22, "pre" should read --per--.

Signed and Sealed this

Twenty-fourth Day of September, 1996

Attest:

BRUCE LEHMAN

*Attesting Officer*    *Commissioner of Patents and Trademarks*